United States Patent
Hoffmann et al.

(10) Patent No.: US 6,713,256 B1
(45) Date of Patent: Mar. 30, 2004

(54) FLUORESCENT ENERGY TRANSFER MEDIATED CHEMICAL ACTIVATION (FETMA) FOR THE ELUCIDATION OF THE THREE-DIMENSIONAL STRUCTURE OF BIOMACROMOLECULES

(75) Inventors: Daniel Hoffmann, Bonn (DE); Ralf Zimmer, Bonn (DE)

(73) Assignee: Fraunhofer Gesellschaft zur Förderung der angewandten Forschung e.V., München (DE)

( * ) Notice: Subject to any disclaimer, the term of this patent is extended or adjusted under 35 U.S.C. 154(b) by 0 days.

(21) Appl. No.: 09/622,161
(22) PCT Filed: Feb. 10, 1999
(86) PCT No.: PCT/EP99/01008
§ 371 (c)(1), (2), (4) Date: Apr. 30, 2001
(87) PCT Pub. No.: WO99/41607
PCT Pub. Date: Aug. 19, 1999

(30) Foreign Application Priority Data

Feb. 14, 1998 (DE) .......................... 198 06 169

(51) Int. Cl.⁷ .......................... C12Q 1/68; G01N 33/53; G01N 33/543; G01N 21/76; G01N 37/00
(52) U.S. Cl. .......................... 435/6; 435/7.1; 435/7.9; 435/7.92; 435/174; 435/968; 435/973; 436/2; 436/56; 436/57; 436/63; 436/164; 436/172; 436/514; 436/518; 436/800; 436/804; 436/805; 436/819; 530/300; 530/350; 250/281
(58) Field of Search .......................... 435/6, 7.1, 7.9, 435/7.92, 174, 968, 973; 436/56, 63, 164, 172, 805, 514, 518, 2, 57, 800, 804, 819; 530/300, 350; 250/281

(56) References Cited

U.S. PATENT DOCUMENTS

| | | | | |
|---|---|---|---|---|
| 5,254,477 A | * | 10/1993 | Walt | 436/172 |
| 5,326,692 A | * | 7/1994 | Brinkley et al. | 435/6 |
| 5,482,867 A | * | 1/1996 | Barrett et al. | 436/518 |
| 5,612,894 A | * | 3/1997 | Wertz | 264/496 |
| 5,622,821 A | * | 4/1997 | Selvin et al. | 435/6 |
| 5,654,419 A | * | 8/1997 | Mathies et al. | 536/25.4 |
| 5,665,966 A | * | 9/1997 | Dahl et al. | 250/281 |
| 6,054,266 A | * | 4/2000 | Kronick et al. | 435/6 |
| 6,123,921 A | * | 9/2000 | Meade et al. | 424/9.363 |
| 6,130,094 A | * | 10/2000 | Waggoner et al. | 436/63 |
| 6,284,544 B1 | * | 9/2001 | Thompson et al. | 436/166 |
| 6,313,274 B1 | * | 11/2001 | Sykes et al. | 436/545 |

FOREIGN PATENT DOCUMENTS

| | | | |
|---|---|---|---|
| EP | 0229943 | | 7/1987 |
| EP | 0 229 943 A2 | * | 7/1987 |
| WO | 9214845 | * | 9/1992 |
| WO | 9848048 | * | 10/1998 |

OTHER PUBLICATIONS

Eisen et al, Eur. J. Bichem 237 514–518 (1996).*
Korutla et al; Thrombosis and Haemostasis (1994) vol. 71 No. 5 pp 609–614.*
Hoffmann, Daniel, et al., "Folding Pathways of a Helix–Turn–Helix Model Protein," *J. Phys. Chem. B*, 101:6734–6740, (1997).
Sun, Jianzhong, et al., "Proximity of Periplasmic Loops in the Lactose Permease of *Echerichia coli* Determined by Site–Directed Cross–Linking," *Biochemistry*, 36:11959–11965 (1997).

* cited by examiner

*Primary Examiner*—Long V. Le
*Assistant Examiner*—Kartic Padmanabhan
(74) *Attorney, Agent, or Firm*—Brobeck, Phleger & Harrison, LLP

(57) ABSTRACT

The present invention relates to a method for the selected chemical activation of photo-activatable cross-linker molecules around ligand binding pockets and fluorescent groups in macromolecules, especially biological macromolecules, by using fluorescent ligands of the macromolecule and by selecting photo-activatable cross-linker molecules having specific activation energies so that a radiationless energy transfer (Förster transfer) from the fluorescent ligands to the cross-linker molecules, which become activated thereby, takes place.

7 Claims, 2 Drawing Sheets

FLUORESCENT ENERGY TRANSFER MEDIATED CHEMICAL ACTIVATION (FETMA) FOR THE ELUCIDATION OF THE THREE-DIMENSIONAL STRUCTURE OF BIOMACROMOLECULES

BACKGROUND OF THE INVENTION

1. Field of the Invention

The present invention relates to a method for the selected chemical activation of photo-activatable cross-linker molecules around ligand binding pockets and fluorescent groups in macromolecules, especially biological macromolecules, by using fluorescent ligands of the macromolecule and by selecting photo-activatable cross-linker molecules having specific activation energies so that a radiationless energy transfer (Förster transfer) from the fluorescent ligands to the cross-linker molecules, which become activated thereby, takes place.

The method according to the invention is preferably used to focus a per se known bioanalytical method for obtaining information about the three-dimensional structure of biomacromolecules to functionally relevant portions of biomacromolecules, such as ligand binding pockets. In this bioanalytical method, the execution of the method according to the invention is followed by: specific digestion of the biomacromolecule, separation of its components by chromatography and mass spectrometry, and a computer simulation for obtaining three-dimensional structural models with the experimentally obtained information as a boundary condition. For refining the structure, the whole procedure may be run in several iterations.

2. Review of the Related Art

Biological macromolecules, such as proteins, ribonucleic acids or macromolecular complexes of different biopolymers, such as ribosomes, are the carriers of the essential biochemical functions of almost all vital processes in biological organisms. Generally, these functions depend on exactly defined three-dimensional structures of the biomacromolecules. From the knowledge of a three-dimensional structure, the functional mechanism can be concluded. This makes three-dimensional structures of biological macromolecules an important source of information for molecular medicine and pharmacology.

Particularly valuable is information about the three-dimensional structure of the binding pockets of biological macromolecules since they are the proper functionally important portions of the macromolecules, because this is where interactions with other, bound molecules, such as ligands or substrates, take place. One of a large number of medicinally relevant examples of how the knowledge of the three-dimensional structure of binding pockets is utilized is the so-called rational design of inhibitors of viral or bacterial enzymes. These inhibitors are designed in such a way that they fit into the binding pockets of the enzymes like keys into locks. Thus, the enzymes become blocked, and the reproduction of the viruses or bacteria is stopped. Such a selective key-lock design is possible only when the three-dimensional structure of the binding pocket is known.

In the prior art, the determination of the three-dimensional structures of biological macromolecules using conventional methods such as X-ray crystallographic analysis or nuclear magnetic resonance has generally been difficult and time-consuming. This has many reasons. In particular, these methods require large (typically millimolar) amounts of the purified macromolecule in a special form, either crystalline or as a concentrated solution. In addition, for solving the three-dimensional structure, further difficulties must be overcome, such as the solution of the so-called phase problem in crystallography. Thus, in total, the elucidation of the three-dimensional structure of a biomacromolecule can take several person-years.

SUMMARY OF THE INVENTION

It has been the object of the invention to provide a method for three-dimensional structural elucidation which requires small amounts of pure macromolecule and can be focused on functionally relevant binding pockets. In addition, the method according to the invention is to be applicable in cases which are particularly difficult to treat with conventional methods. These include, for example, membrane proteins and large globular proteins and complexes which are difficult to purify and difficult to crystallize.

In a first embodiment, the method according to the invention for the three-dimensional structural elucidation of macromolecules (M) is characterized in that a ligand (F) capable of fluorescence with a fluorescence frequency within a range of from $v_1$ to $v_2$ is introduced into said macromolecule (M), or its spatial position relative to the macromolecule (M) is determined by per se known methods; one or more photoactivatable bifunctional cross-linkers C, C', C" with their respective excitation frequencies within the range of from $v_1$ to $v_2$ are covalently bound between the non-photoactivatable end S of the cross-linker C, C', C" and suitable functional groups m of the macromolecule M with exclusion of light; said macromolecule M is irradiated above the frequency interval $v_1$ to $v_2$ with a frequency $v_Q$ wherein the photoactivatable end A and/or A' of the cross-linker C and/or C" is activated for reaction with the surface of macromolecule M by means of radiationless transfer (Förster transfer) to neighboring cross-linkers C and/or C", and reacts with the surface of macromolecule M depending on the distance of said ligand (F) capable of fluorescence; and the groups linked together in pairs are identified by bioanalytical methods, especially specific digestion of macromolecule M, the digestion fragments are separated, especially by their mass, and spatial neighboring relationships are determined by calculation.

Further embodiments of the invention can be seen, in particular, from the dependent claims.

BRIEF DESCRIPTION OF THE DRAWINGS

In FIG. 1a, B and F are firmly connected; direction-dependent blanking out of A groups can occur (in contrast to A, A' is not activated, despite the fact that distance FA is equal to distance FA').

In FIG. 1b, B and F are linked through the flexible joint L. F can orient itself freely. There is no blanking out as in FIG. 1a.

Figure 2A:
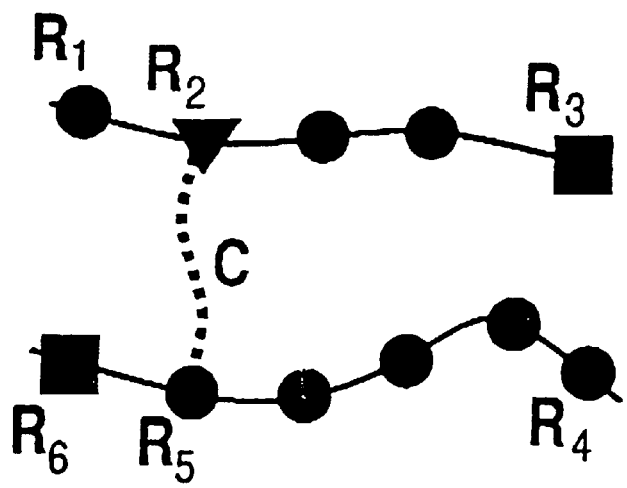
FIG. 2a shows this fragment as a component of the digestive mixture of the macromolecule after cross-linking.
Figure 2B:
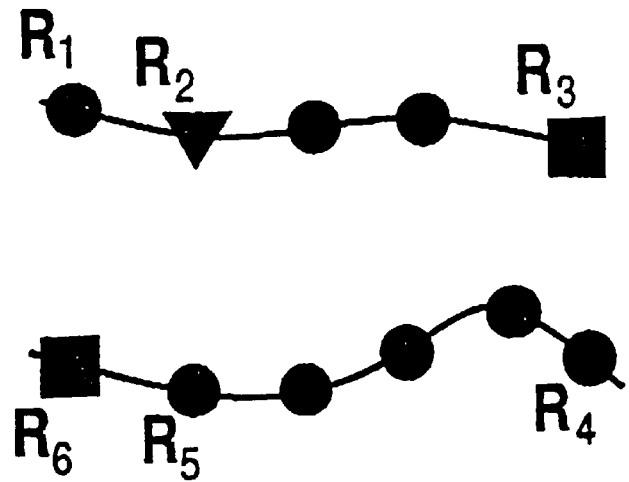
FIG. 2 describes the composition of the mixture of the macromolecular fragments after digestion of the macromolecule (schematically). The lytic reagent has specifically cleaved between monomers of the type of monomer R1 or R4 (circles) and monomers of the type of monomer R3 or R6 (squares). The cross-linker molecule C binds specifically to residues of the type of monomer R2 (triangles) and, after photoactivation, non-specifically to spatially neighboring groups, such as monomer R5 in this case.

Instead of the fragments shown in FIG. 2a, FIG. 2b shows two separated fragments occurring in the digestive mixture of the macromolecule without a cross-linker.

DETAILED DESCRIPTION OF THE INVENTION

The method according to the invention makes use of the following physical properties and effects:

The specific spatially defined binding of the fluorescent ligand (with the fluorophor F in FIG. 1a and FIG. 1b) to the macromolecule. Instead of a ligand, a fluorescent group naturally present in the macromolecule (for example, indole groups of tryptophan in proteins) may also be used if the three-dimensional structure of its environment is to be examined.

The specific covalent bonding of the cross-linker molecule to particular accessible portions of the macromolecule through specific functional groups (S in FIG. 1a and FIG. 1b) at one end S of the cross-linker molecules C, C', C". At the other end A, A', A" of the cross-linker molecules, there are photoactivatable groups (acceptors A in FIG. 1a and FIG. 1b).

The excitation of the fluorophor of ligand F or suitably modified ligands or fluorescent groups.

The radiationless, efficient transfer (Förster transfer) of the fluorescent energy from the bound fluorophors or those naturally present in the macromolecule M to acceptors A and/or A' of cross-linker molecules C spatially neighboring the fluorophors.

The chemical activation of acceptors A and/or A' by the fluorescent energy.

The non-specific covalent bonding of the activated acceptors A and/or A' to immediately neighboring groups of macromolecule M (cross-linking).

It is important to the method according to the invention that the following conditions be met:

The absorption frequency $v_Q$ of the fluorophors F must be within a frequency interval in which a significant excitation of the photoactivatable groups does not occur.

The emission frequency of the fluorophors F must be within a frequency interval $v_1$ to $v_2$ in which a significant portion of the photoactivatable groups A, A', A" on the cross-linker molecules is activated.

These two conditions can be met by suitably selecting the ligand F and the cross-linker molecule C. An essential difference between the method of the invention and per se known methods of cross-linking with photoactivatable groups lies in the indirect activation through excitation of the fluorophor, followed by Förster transfer to the photoactivatable groups A and/or A'. This enables a space-resolved activation around the specifically bound fluorophor F, in other words, focusing of the activation on the environment of functionally relevant binding pockets or groups. Thus, the method according to the invention achieves a new quality in biological structural research.

The first step of the method according to the invention is preferably followed by a per se known bioanalytical process step to convert the result of the method according to the invention into information about the three-dimensional structure of the macromolecule. The crucial idea in the method according to the invention is the fact that only those groups on the accessible surface of macromolecule M are linked by cross-linker molecules C as have a mutual spatial distance which is smaller than the maximum length of the cross-linker molecule. Thus, if the groups linked together in pairs through cross-linker molecules C can be identified, their largest possible spatial distance is known, and a piece of information about the three-dimensional structure has been obtained. Said per se known process step which preferably follows the first process step comprises the following elements:

Specific digestion (proteolysis, nucleolysis) of the macromolecule.

Separation of the fragments from the digestion, especially by their mass (HPLC, MALDI-TOF mass spectrometry).

Determination of spatial neighboring relationships by calculation from the experimental results, and computer simulation of the macromolecule with the experimentally determined neighboring relationships as boundary conditions. This step yields one or more three-dimensional structural models.

To determine the global three-dimensional structure of macromolecules M, the cross-linking according to the invention is preferably combined with the direct photoactivation of cross-linkers C and with the per se known method of cross-linking with bifunctional cross-linker molecules C.

For achieving a stepwise refinement of the three-dimensional structural model, a repeated application of the method according to the invention in combination with the per se known methods preferably following it as set forth above is recommendable. In each cycle, different parameters can be set to obtain new independent pieces of structural information. In particular, different cross-linker molecules and digestive reagents can be selected in each cycle.

1. Specific Spatially Defined Binding of the Ligand to the Macromolecule

A fluorophor F specifically bound to the macromolecule M is the first essential component of the method according to the invention. The method according to the invention provides information about the three-dimensional structure of macromolecule M in the spatial environment of this fluorophor F. For example, if the three-dimensional structure in and around the substrate binding pocket of an enzyme is to be examined, possible carriers for the fluorophor F include fluorescent inhibitors or substrate analogues and, in very slowly working enzymes, also the substrate itself if it is fluorescent. In addition, fluorescent cofactors (for example, flavin in cholesterol oxidase) or fluorescent effectors (for example YC-1 as an effector of soluble guanylyl cyclase) can be used, as well as fluorescent groups covalently bound to the macromolecule, such as tryptophanes in proteins. In all cases, it is important that the position of the fluorophor F relative to the macromolecule M be defined as exactly as possible, which is naturally met in the examples mentioned.

Figure 1A:
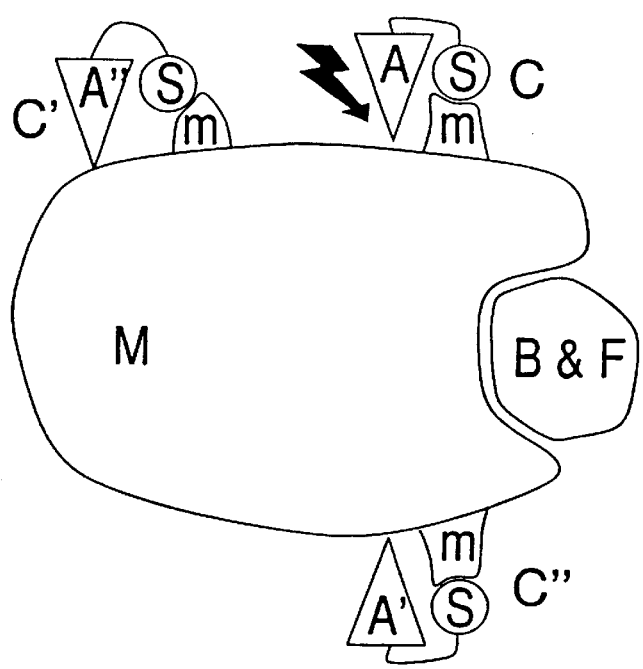
FIGS. 1a and 1b describe the chemical activation by Förster transfer. The energy is transferred from the excited fluorophor F to neighboring photoactivatable groups A and/or A'. There is no significant transfer to more remote photoactivatable groups A". M stands for macromolecule; B stands for the binding portion of the fluorescent ligand; F stand for fluorophor; m stands for specific chemical groups on M; S stands for groups on cross-linkers which specifically bind covalently to m groups; L stands for a flexible joint between B and F, for example, an alkyl chain.

In accordance with the method of the invention, a distinction is to be made between two kinds of linking of the fluorophor with the residue of the group specifically bound to the macromolecule (FIG. 1):

The fluorophor F is rigidly linked with that portion B of the molecule which is responsible for the specific binding to macromolecule M (FIG. 1a).

Figure 1B:
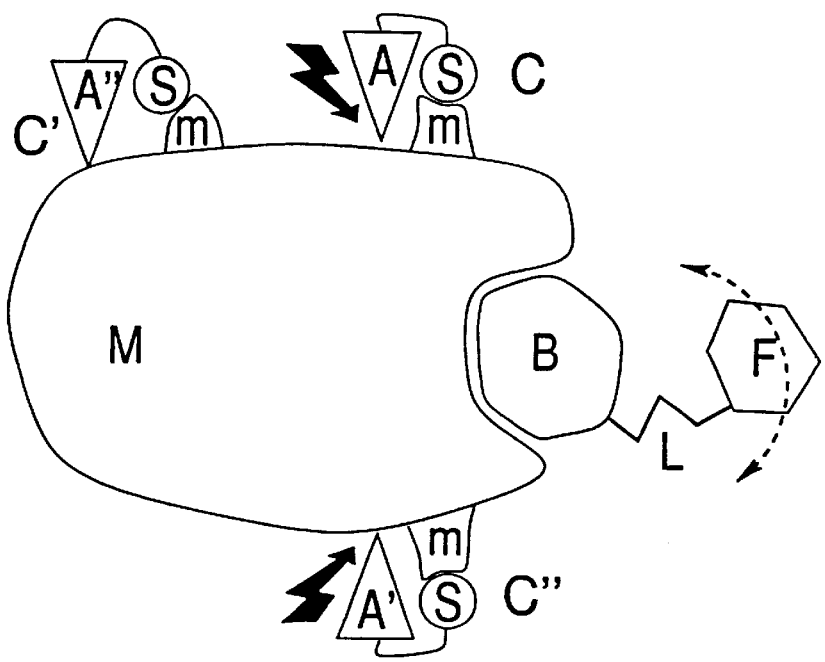

The fluorophor F is flexibly linked (for example, through an alkyl chain) with the portion B which is responsible for the specific binding to macromolecule M (FIG. 1b). Due to the flexible joint L, the fluorophor F can rotate freely relative to B and M.

As set forth in more detail below under item 4, both possibilities yield different kinds of information about the three-dimensional structure of the macromolecule which complement each other.

Thus, to conclude, the first step of the method according to the invention is the specific binding of the fluorophor-carrying ligand F to the macromolecule M except when a fluorophor F already present in the macromolecule M is employed. For example, if the environment of the effector binding pocket of soluble guanylyl cyclase (sGC) is to be examined, the fluorescent ligand YC-1 can be used as a probe. YC-1 is added to an aqueous solution of sGC and binds with high affinity within a specific binding pocket of sGC.

2. Specific Chemical Binding of the Cross-linker C

The second step of the method according to the invention is the chemically specific covalent bonding between the non-photoactivatable end A and/or A' of the cross-linker (S in FIG. 1), on the one hand, and suitable functional groups (m in FIG. 1) on the surface of the protein, on the other hand. Thus, the selected cross-linker C is added to the above solution which already contains the complexes between the macromolecule M and the fluorescent ligand F. For example, 4-[p-azidosalicylamido]butylamine (ASBA) may be used as the cross-linker C. With its amino end, ASBA specifically reacts with carbonyl and carboxy groups on the surface of the macromolecule M. It is important to allow the reaction to proceed in the dark in order to prevent a premature photoactivation of ASBA. In addition, the solution must be adjusted in such a way that while a reaction of ASBA with the macromolecule M occurs, the macromolecule M is not denatured.

3. Excitation of the Fluorophor F

The third step of the method according to the invention is the excitation of the fluorophor F by the irradiation of light the frequency of which corresponds to the absorption frequency of the fluorophor F. As described above, a direct activation of the photoactivatable end A, A', A" of the cross-linker C must not occur at this frequency, which can generally be ensured by selecting appropriate cross-linkers C. For example, the photoactivatable portion of ASBA absorbs between 250 nm and 320 nm and can thus be excited at the emission wavelength of YC-1, which lies in the same range.

Attention must be paid to the fact that the absorption and emission spectra of the ligand F exhibiting fluorescence within the binding pocket or of the fluorescent group can be shifted with respect to the spectra of the free fluorophors F in an aqueous or other solution depending on their environments (solvatochromism). This can be the case, in particular, when the binding and fluorescent portions of ligand F are rigidly linked to one another (FIG. 1a). The solvatochromic shift must be considered when the cross-linker molecule C is selected, since the fluorescent energy is to be transferred from the fluorophor F to the photoactivatable group of the cross-linker C, and therefore, the photoactivatable group must exhibit a significant absorption at the emission frequency of the fluorophor F. When the absorption and emission frequencies of the fluorophor F are not known, they can be determined by fluorescence spectroscopy; the cross-linker C is then selected using the thus measured spectra. Alternatively, several types of cross-linkers C which absorb in different frequency intervals, but not at the frequency of the light irradiated from outside ($v_O$) for exciting the fluorophor F, may be used in parallel. If the solvatochromic shift of the fluorophor F as a function of the polarity of the surrounding medium is known, the character of the binding pocket (polar or non-polar) can be concluded from the actually observed solvatochromic shift; thus, a first piece of structural information about the binding pocket would already have been obtained.

4. Chemical Activation through Radiationless Transfer of the Fluorescent Energy to Spatially Neighboring Specific Acceptors The next step of the method according to the invention is the chemical activation of those photoactivatable groups A and/or A' of the cross-linker molecules C and/or C" which are in a spatial proximity to the fluorophor F. The energy necessary for activation is transferred in a radiationless manner by Förster transfer from the excited fluorophor F to the photoactivatable groups A and/or A'. The transfer rate decreases proportionally with the sixth power of the reciprocal distance from F to A, A', A". High transfer rates typically occur if the distance between F and A, A', A" is on the order of 1 nm. Towards larger distances, the transfer rate is rapidly decreased.

The transfer rate depends not only on the distance between the fluorophor F and the photoactivatable group A, A', A", but also on the angle between the emission transition dipole moment of F and the absorption transition dipole moment of A, A', A". The highest rates are achieved when both dipole moments are parallel, and the rates are zero when they are orthogonal. In the method according to the invention, this effect is important when the binding of fluorophor F is completely rigid relative to macromolecule M (FIG. 1a). In this case, only those photoactivatable groups A are activated which both are in a spatial neighboring relationship with F and have a suitable orientation relative to F. This effect generally does not occur since the photoactivatable groups mostly do not exhibit any preferred orientation prior to activation. If the effect should nevertheless occur (FIG. 1a, only A is activated while A' is not, although both groups are at the same distance to F), the use of a ligand having a flexible joint L between the binding portion of ligand B and the fluorophor F (FIG. 1b) is recommendable. Since F can rotate freely then, a blanking out of photoactivatable groups due to the orientation dependence is avoided, i.e., only the distance between F and A determines the activation.

By the radiationless Förster transfer, the excitation energy is transferred from F to A and/or A' very much more efficiently than it would be transferred by fluorescent emission from F and reabsorption by A and/or A'. Thus, the latter process does not result in a significant activation of A and/or A', which facilitates the interpretation of the experiments.

5. Chemically Non-specific Reaction of the Photoactivatable Groups of the Cross-linker Molecules C and/or C"

The next step of the method according to the invention is the chemical reaction of the activated photoactivatable groups A and/or A' of the cross-linker molecules C and/or C" with groups on the surface of the macromolecule M. These reactions are relatively non-specific chemically, i.e., the activated groups A react with those groups on M, mostly irrespective of their chemical nature, which are in a close spatial neighboring relationship with the activated groups A and/or A'. After the reaction, the cross-linker molecules C and/or C" form covalent bridges between portions of the surface of macromolecule M. The maximum length of these bridges can be influenced through the length and rigidity of cross-linker C. For ASBA, this length is 1.6 nm.

Generally, only those cross-linkers C are reactive towards macromolecule M whose distance to the fluorophor F is small. Thus, the identification of the reacted groups of macromolecule M yields another piece of information about the three-dimensional structure of macromolecule M, namely an upper limit for the spatial distances between the fluorophor F and the groups on the surface of macromolecule M which have reacted with the photoactivated groups A and/or A' of the cross-linker molecules C and/or C".

For converting the results of the application of the method according to the invention into three-dimensional structural information, the method according to the invention is preferably used with per se known bioanalytical and computational methods which will be illustrated in the following.

6. Specific Digestion

The macromolecules M with associated fluorophors F and cross-linkers C, C', C" are specifically digested, i.e., cleaved with lytic reagents which react at specific motifs on the macromolecules M. If macromolecule M is a protein, for example, proteases such as trypsin can be used for this purpose. Trypsin cleaves polypeptide chains specifically after lysines or arginines. For comparison, the same macromolecules M are digested in another assay without cross-linkers C, C', C". From both digestion assays, mixtures portions of macromolecule M with or without attached cross-linkers C, C', C" are respectively obtained. Those portions of molecule M are important which are divided into two separate fragments after digestion without cross-linkers C, C', C" (FIG. 2b) while they are kept together by cross-linkers C and/or C" after application of the method according to the invention (FIG. 2a). In the native conformation of macromolecule M, such portions are at a spatial distance which is given by the length of the cross-linker molecule C.

7. Separation and Identification of the Macromolecular Fragments

For the creation of a three-dimensional structural model, information about which portions of macromolecule M were linked by cross-linker C is still necessary. Thus, the mixtures of the above fragments must be separated, and the individual fragments identified, i.e., assigned to sequence pieces of the macromolecular polymer (this requires that the sequence of the polymer, for example, in the case of a protein, the sequence of the amino acids, is known). For the separation and identification in the method according to the invention, per se known methods such as HPLC and MALDI-TOF mass spectrometry are preferably employed. The fragments can generally be identified by their masses.

The mass spectrum of the digested macromolecule M without cross-linkers C, C', C" is compared with the mass spectrum of the digested macromolecule M with cross-linkers C, C', C". In the latter, masses appear which correspond to the sum of the masses of the fragments linked through cross-linkers C and/or C" plus the mass of cross-linker C. These fragments are identified by their masses. Thus, it is known that these fragments are at a distance in the native structure of macromolecule M which is shorter than the maximum length of cross-linker C. In addition, it is known that the two interconnected portions and the space between them must be accessible to the cross-linker molecule C and/or C". Both are important pieces of information on the three-dimensional structure of the macromolecule.

8. Computational Prediction of the Three-dimensional Structure of the Macromolecule Using the Experimentally Determined Pieces of Information as Boundary Conditions Now, the above obtained structural information remains to be converted into a three-dimensional structural model. Thus, the experimental results obtained by the method according to the invention are taken into account as geometric boundary conditions in per se known methods for the computer simulation (D. Hoffmann, E. W. Knapp; J. Phys. Chem. B 101: 6734–6740, 1997) of macromolecule M.

Alternatively, these boundary conditions may also be employed in distance-geometrical methods, such as threading methods for protein structure predictions. In any case, the result of this computational step is a three-dimensional structural model or several three-dimensional structural models of macromolecule M.

9. Further Runs with Other Cross-linkers and Other Lytic Reagents

If a refinement of the three-dimensional structural model is desired or if the number of three-dimensional structural models consistent with the experimental boundary conditions is to be reduced, the respective process steps can be performed with different reagents. In particular, cross-linkers C having different lengths or chemical specificities can be used, and different digestion reagents can be employed. Iteration is done until a further refinement is no longer desired or possible.

What is claimed is:

1. A method to assist in three-dimensional structural elucidation of a macromolecule, characterized in that
   a) a ligand is introduced into said macromolecule, or its spatial position relative to the macromolecule is determined, said ligand fluorescing upon excitation with a fluorescence frequency within a range of from $v_1$ to $v_2$;
   b) one or more photoactivatable bifunctional cross-linkers are covalently bound to functional groups of the macromolecule by reaction with a non-photoactivatable reactive group on the cross-linkers, each cross-linker having a photoactivatable end with an excitation frequency within said range of from $v_1$ to $v_2$, and a non-photoactivatable end, wherein said non-photoactivatable end of the cross-linker is covalently bound to the macromolecule;
   c) said macromolecule is irradiated with light having a frequency $v_Q$, which is above the frequency interval $v_1$ to $v_2$, wherein the photoactivatable end of the cross-linker is activated for reaction with a surface of the macromolecule by means of radiationless Förster transfer from said ligand to neighboring cross-linkers, which react with the surface of the macromolecule depending on the distance of said ligand from said neigboring cross-linkers, wherein groups linked together in pairs are formed; and
   d) groups linked together by said cross-linkers are identified for determination of spatial neighboring relationships between linked groups.

2. The method according to claim 1, characterized in that said macromolecules are selected from proteins, ribonucleic acids or macromolecular complexes of different biopolymers.

3. The method according to claim 1, characterized in that direct photoactivation of cross-linkers occurs simultaneously with reaction of bifunctional cross-linkers binding to the macromolecule with chemical specificity.

4. The method according to claim 1, characterized in that 4-[p-azidosalicylamido]butylamine is used as the cross-linker.

5. The method according to claim 1, wherein said groups linked in pairs are identified by bioanalytical methods comprising specific digestion of the macromolecule, and digestion fragments are separated.

6. The method according to claim 5, characterized in that the digestion fragments are separated by their masses.

7. The method according to any one of claims 1–6, characterized in that the method is repeated several times, optionally using different ligands, cross-linkers and/or digestion reagents.

* * * * *